United States Patent
Brooks

(10) Patent No.: US 6,824,763 B2
(45) Date of Patent: Nov. 30, 2004

(54) ANTI-FUNGAL POWDER HAVING ENHANCED EXCIPIENT PROPERTIES

(75) Inventor: JoAnn Adele Brooks, Arlington, TX (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 146 days.

(21) Appl. No.: 10/161,157

(22) Filed: May 30, 2002

(65) Prior Publication Data

US 2003/0224063 A1 Dec. 4, 2003

(51) Int. Cl.$^7$ .............. A61K 7/00; A61K 7/06; A61K 7/035; A61K 31/74
(52) U.S. Cl. .......... 424/69; 424/70.11; 424/70.12; 424/78.03; 424/78.07; 424/401
(58) Field of Search .............. 424/69, 400, 404, 424/489, 490, 496

(56) References Cited

U.S. PATENT DOCUMENTS

| | | | |
|---|---|---|---|
| 4,801,445 A | 1/1989 | Fukui et al. | |
| 4,818,614 A | 4/1989 | Fukui et al. | |
| 4,869,904 A | 9/1989 | Uekama et al. | |
| 4,880,774 A | 11/1989 | Joukou et al. | |
| 5,246,780 A | 9/1993 | Farer et al. | |
| 5,324,718 A | 6/1994 | Loftsson | |
| 5,422,347 A | 6/1995 | Bononi | |
| 5,472,954 A | 12/1995 | Loftsson | |
| 5,476,852 A | 12/1995 | Cauwenbergh | |
| 5,607,980 A | 3/1997 | McAtee et al. | |
| 5,643,672 A | 7/1997 | Marchi et al. | |
| 5,658,956 A | 8/1997 | Martin et al. | |
| 5,662,932 A | 9/1997 | Amselem et al. | |
| 5,665,364 A | 9/1997 | McAtee et al. | |
| 5,696,164 A | 12/1997 | Sun et al. | |
| 5,723,420 A | 3/1998 | Wei et al. | |
| 5,800,816 A | 9/1998 | Brieva et al. | |
| 5,811,111 A | 9/1998 | McAtee et al. | |
| 5,814,330 A | 9/1998 | Putteman et al. | |
| 5,993,967 A | 11/1999 | Brotzman, Jr. et al. | |
| 6,004,584 A * | 12/1999 | Peterson et al. ............. | 424/489 |
| 6,033,781 A | 3/2000 | Brotzman, Jr. et al. | |
| 6,042,845 A | 3/2000 | Sun et al. | |
| 6,046,177 A | 4/2000 | Stella et al. | |
| 6,083,529 A * | 7/2000 | Manzo et al. ............... | 424/450 |
| 6,156,430 A | 12/2000 | Weber et al. | |
| 6,248,363 B1 | 6/2001 | Patel et al. | |
| 6,514,504 B1 * | 2/2003 | Yen et al. .................... | 424/401 |
| 2003/0087776 A1 * | 5/2003 | Heltovics et al. ........... | 510/101 |

FOREIGN PATENT DOCUMENTS

| | | |
|---|---|---|
| EP | 0 314 206 B1 | 10/1993 |
| JP | 07115003 * | 11/1996 |
| WO | WO 97/40816 A1 | 11/1997 |
| WO | WO 99/21532 A1 | 5/1999 |
| WO | WO 00/72818 A1 | 12/2000 |
| WO | WO 01/00151 A1 * | 1/2001 |
| WO | WO 01/01955 A1 * | 1/2001 |
| WO | WO 01/13968 A1 | 3/2001 |

* cited by examiner

Primary Examiner—Thurman K. Page
Assistant Examiner—S. Tran
(74) Attorney, Agent, or Firm—Pauley Petersen & Erickson

(57) ABSTRACT

A body powder is disclosed. The body powder includes a topical anti-fungal agent in combination with at least two excipients. One excipient is a boron nitride particulate material coated with a silicone compound. The other excipient is a fragrance molecularly entrapped within a cyclodextrin compound.

16 Claims, No Drawings

ANTI-FUNGAL POWDER HAVING ENHANCED EXCIPIENT PROPERTIES

BACKGROUND OF THE INVENTION

Cutaneous mycoses, also called dermatophytes or tineas, represent the most common fungal diseases in humans. Typical fungal infections in humans may appear as superficial and/or cutaneous presentations characterized by itching, swelling, redness, irritation, skin odor, and/or weeping, cracking or fissuring of the epidermis. Individuals, particularly the elderly or chronically ill and those who are obese, suffer from incontinence, or are immunocompromised, are especially prone to these types of infections. Most of these infections are chronic and difficult to cure.

Fungal infections are exacerbated by humid conditions that allow the fungi to proliferate. For humans, humid conditions typically develop when moisture in the form of sweat or urine becomes trapped between the clothing and the body and is not effectively wicked away, dried or evaporated from the skin surface. Certain garments such as incontinent products in the form of briefs, pads, pants, shields or undergarments or other products like training pants or diapers can increase the level of humidity in the inguinal groin, perineum and waist regions of the wearer and create optimal conditions for fungal growth. Moisture also can be physically trapped due to reduced air circulation in skinfolds in the perineum, beneath the breast, or in the inguinal area of the groin.

Other common skin flora can also exacerbate cutaneous mycoses by irritating or breaking down the epidermis. For example, bacteria are known to produce chemical byproducts including ammonia, dimethyl sulfide, trimethylamine, and isovaleric acid or other short chain organic acids through the biotransformation of aprocrine sweat, urine and skin proteins. Such byproducts can be quite irritating to the epidermis especially when the skin is already compromised due to dehydration or fungal infection. In addition, these byproducts can be very malodorous causing embarrassment and discomfort for the sufferer and those close to them.

Avoiding the proliferation of fungi and bacteria can minimize the development of common skin irritants and subsequent damage to the skin. Many types of skin care products such as ointments, oil-in-water emulsions, creams, loose powders, and lotions have been used to treat areas of the body that need protection from moisture. Many of these products contain topical anti-fungal agents that, when applied to the skin, can destroy or inhibit the proliferation of the fungi at the root of the infection. Often, these products also include a fragrance or perfume to mask or eliminate unpleasant body odors. However, fragrances or perfumes can be irritating to the skin and can exacerbate compromised skin.

Loose powders have been found to be particularly effective for removing or absorbing moisture from the skin surface. In addition, coating the skin with powdered materials such as corn starch can reduce friction on the skin, due to obesity or shifting or tightness of garments, which can irritate or further exacerbate compromised skin. Furthermore, coating the skin with a loose powder can reduce the probability of adhesion and subsequent colonization of skin fungi and/or bacteria. However, these types of materials often produce a gummy and/or unpleasant feel when exposed to moisture,

SUMMARY OF THE INVENTION

Now, an anti-fungal body powder having enhanced excipient properties has been developed. The powder delivers a topical anti-fungal agent to the skin to destroy and/or inhibit proliferation of fungi while minimizing irritation to compromised skin and reducing odor associated with cutaneous mycoses and/or bacterial biotransformation byproducts. The body powder includes a Food and Drug Administration (FDA) approved topical anti-fungal agent that has been proven effective against the types of fungi commonly associated with skin infections. The body powder also includes at least two excipients that enhance the effectiveness and feel of the body powder.

A boron nitride particulate material, desirably in the form of small micronized particles, is coated or impregnated with a silicone compound and is used to reduce and/or prevent adhesion of fungi and bacteria on the skin which in turn reduces colonization of these microorganisms. The silicone coating helps to reduce the perception of grittyness often associated with ceramic powders and provides enhanced slip and lubricity on the skin surface. Additionally, selecting a boron nitride material that has a flat plate particle morphology assists in protecting irritated and/or infected skin. In use, the flat plate particles can order or arrange themselves in closely aligned groups that form a sheet or protectant coating on the skin surface reducing the ability of irritants or fungi from reaching the skin surface.

A fragrance is added to the body powder to assist in reducing the appearance or strength of odors often associated with fungal infections and the biotransformation of apocrine sweat. Because fragrances can be irritating to the skin, especially irritated and/or compromised skin, the fragrance is molecularly entrapped within a cyclodextrin compound to reduce the level of contact between the fragrance and the skin. Additionally, the fragrance usually includes chemicals that are volatile and dissipate over time. Molecularly entrapping the fragrance within a cyclodextrin compound extends the life of the fragrance both in use and in storage. Desirably, the fragrance includes an essential oil that also assists in extending the life of the fragrance and may provide some anti-bacteriostatic functionality.

Preservative compounds and additional excipients such as talc, clays, modified corn starch, acrylic acid co-polymers, maleic acid, stearates, oxides or a combination thereof can be added to the body powder. The preservatives and excipient can further enhance the powder's ability to absorb moisture, inhibit the formation of malodorous compounds, and inhibit the proliferation of bacteria and fungi. For example, preservatives such as disodium ethylene diamine tetraacetic acid acts as enzyme inhibition chemical by providing chelating agents to block the production of malodorous bacterial byproducts. Talc, clays, and modified corn starches assist in the absorption of sweat and moisture keeping the skin drier and reducing the gummy feel often associated with powders when they become wet. Acrylic acid co-polymers can be used to absorb moisture as well as to regulate the pH of the body powder and impart additional bacteriostatic and/or anti-fungal properties to the body powder. Maleic acid can be used to control the pH of the body powder by offsetting the high pH levels associated with talc.

DETAILED DESCRIPTION

The body powder of the present invention includes a topical anti-fungal agent in combination with at least two excipients. Suitably, the body powder has the ability to inhibit and/or reduce the proliferation of fungi on the skin surface that contribute to irritation and/or infection of the epidermis. Desirably, the body powder also assists in controlling and/or preventing the formation of malodorous compounds by inhibiting the proliferation of bacteria and fungi.

Advantageously, the body powder has a smooth silky texture that forms a protective layer on the skin surface and effectively absorbs moisture while avoiding a developing a gummy or tacky feeling. More advantageously, the body powder is a dry, particulate material at room temperature that is resistant to clumping or caking when exposed to humid conditions. Suitably, the individual compounds included in the body powder are blended in a dry, particulate form thereby eliminating the need for drying, grinding or sieving to achieve the end product. As used herein "dry, particulate state" means that the individual compounds exhibit a moisture content less than about 10% by weight of the compound and have a particle size of from about 10 microns and about 80 microns.

Additionally, the body powder desirably contains a fragrance that has a long life both in use and in storage that does not contribute to the irritation of the skin surface. The body powder should demonstrate a fragrance stability of up to 2 years or more. Suitably, the body powder should have a pH between about 5 to about 7 so that it is non-irritating to the skin. Desirably, the body powder has an extended wear time and remains present on the treated skin for at least about 12 hours, and up to about 72 hours, absent bathing.

As used herein, the term "topical anti-fungal agent" is used to identify materials, also known as active ingredients, which have been approved by the Food and Drug Administration (FDA) as effective for over-the-counter treatment of cutaneous and superficial dermatophytic infections. The term "excipient(s)" is used to designate a material other than an anti-fungal agent or a preservative that may or may not contribute to the inhibition of fungi on the skin surface and which can provide other important performance enhancing attributes such as moisture absorbency, odor control, or improved processibility in manufacturing. The term "biotransformation" is used to describe the various chemical and biological processes by which compounds that occur naturally in apocrine sweat, urine and feces are converted to compounds which contribute to development of unpleasant and/or undesirable body odors. The term "fragrance stability" means that the fragrance in the body powder is detectable by a trained olfactory sensory analyst after aging or storage of the body powder for up to 2 years or more. The term "thermostable" is used to define materials that do not produce undesirable chemical breakdown products or significantly volatize or dissipate upon repeated exposure to elevated temperatures above room temperature or humidity above 50 percent.

The body powder of the present invention includes a topical anti-fungal agent. The topical anti-fungal agent should be effective against common fungi that affect the smooth or bare parts of the body (tinea corporis). Such fungi include *Trichophyton rubrum*, *Trichophyton mentagrophytes*, and *Microsporun canis*. Suitable anti-fungal agents for use in the present invention include miconazole compounds (1-(2-((2,4-dichlorophenyl)-2-(2,4-dichlorophenyl)-methoxy)ethyl)-1-imidazole) and econazole compounds 1-(2-((4-chlorophenylmethoxy)-2-(2,4-dichlorophenyl)ethyl)-1H-imidazole). Other suitable topical anti-fungal agents known to those skilled in the art may also be used. Desirably, the topical anti-fungal agent included in the body powder is miconazole nitrate. More desirably, the miconazole nitrate is present in a concentration of about 2% by weight of the body powder.

The body powder of the present invention also includes at least two excipients in combination with the topical anti-fungal agent. One of the excipients is a boron nitride particulate material (small micronized particles) that is coated or impregnated with a silicone compound. The boron nitride particles are desirably coated with a silicone compound for several reasons. Using silicone-coated particles improves the slip and lubricity of the powder providing a silkier feeling on the skin. The improved slip and lubricity also provides for easier processing in production by reducing adhesion of the particles to themselves and to other compounds included in the body powder. The silicone coating also reduces the gritty feeling often associated with ceramic powders such as boron nitride making them less irritating to the skin. Furthermore, incorporating the silicone-coated boron nitride particles into the body powder assists in reducing and/or inhibiting the proliferation of fungi and/or bacteria by inhibiting adhesion of the microorganisms to the skin surface. Uncoated boron nitride powders have been shown to denature and/or deteriorate other compounds, such as fragrances, used in body powder formulations. Thus, using silicone-coated boron nitride materials also contributes to the long-term stability and shelf life of the body powder of the present invention.

Advantageously, the silicone coated boron nitride material has a particle size from about 10 microns to about 80 microns. More advantageously, the silicone coated boron nitride material has a particle size of from about 10 microns and about 50 microns. Most advantageously, the silicone coated boron nitride particles have a particle size from about 10 microns to about 25 microns. Suitably, the silicone coated boron nitride particles should be white and odorless. More suitably, the silicone coated boron nitride material should contain less than 1 part per million by weight of the boron nitride material mercury, arsenic and lead. Desirably, the silicone coated boron nitride material should have microbial limits including a combined microbial count of less than about 500 microorganisms per gram of silicone coated boron nitride material and the absence of gram negative bacteria.

Suitable silicone compounds for coating the boron nitride particles include polydimethylsiloxane (also known as dimethicone) and polymethylhydrogen siloxane (also known as methicone). One example of a polydimethylsiloxane coated boron nitride material that is suitable for use in the present invention is available under the registered trademark TRES BN UHP1106 from Carborundum Corporation, Boron Nitride Division, having an office at 168 Creekside Drive, Amhearst, N.Y., 14428. A suitable polymethylhydrogen siloxane coated boron nitride particulate material is available under the registered trademark TRES BN UHP1107 also from Carborundum Corporation.

Desirably, the silicone coated boron nitride material is present in a concentration of from about 2% to about 7% by weight of the body powder. More desirably, the silicone coated boron nitride material is present in a concentration of from about 3% to about 5% by weight of the body powder. Most desirably, the silicone coated boron nitride material is present in a concentration of about 4% by weight of the body powder.

The second excipient in combination with the topical anti-fungal agent is a fragrance that is molecularly entrapped within a cyclodextrin compound also known as a fragrance inclusion complex. The use of a fragrance inclusion complex is desirable to reduce the degree of volatilization of the fragrance upon repeated exposure to elevated temperatures and/or humidity. The fragrance inclusion complex also serves to protect the chemical integrity of the fragrance notes until use and additionally protects the skin from direct contact with fragrance.

Generally, the fragrance will contain a blend of aroma compounds and inert carrier compounds that do not contribute to the scent of the fragrance. Aroma compounds usually include compounds described as having top notes, middle notes and/or base notes. Top note compounds are the least resistant to heating and will generally flash off or volatilize quickly upon exposure to elevated temperatures. Middle note compounds, such as aldehydic lifters, are more stable and longer lasting, but are still prone to dissipation over a relatively short period of time or upon repeated exposure to elevated temperatures. Base note compounds are those compounds often characterized as having a "heavy" scent and are the most resistant to dissipation over time, lingering for long periods. One class of base note compounds includes essential oils. Generally, a fragrance may be made of from about 5% to about 50% aroma compounds. Typically, a fragrance may include from about 50% to about 95% inert carrier compounds. Suitable inert carrier compounds can include dipropylene glycol.

Desirably, the fragrance includes at least one essential oil. More desirably, the fragrance includes at least one essential oil that is thermostable up to at least about 165° F. (about 75° C.). By selecting a fragrance that includes at least one essential oil that is thermostable up to about 165° F. (about 75° C.) the fragrance will remain detectable after exposure to heat. Suitable essential oils include ylang ylang, coriander, grapefruit, lavender, white thyme, mandarin orange oil, tuberose, jasmine, lavadin, galbanum, rose absolute, clove leaf, eucalyptus, and geraniol. Other essential oils suitable for use in the present invention include sandalwood, musk, orris root, rose, lily of the valley, bergamot, orchid, ginger, nutmeg, lemongrass, tumeric, rosemary, clove, chamomile, achillea, thulasi and cedar. Additionally, other essential oils known to those skilled in the art can also be used. Desirably, the fragrance contains from about 0.01% to about 1% of an essential oil. Suitably, the body powder includes between about 0.3% to about 1% of fragrance by weight of the body powder.

The fragrance inclusion complex is typically formed by dispersing and mixing a liquid fragrance with a powdered cyclodextrin compound. The fragrance is entrapped within the open cyclodextrin structure forming a powder-dispersible paste. The resulting powder-dispersible paste is mixed into the powder matrix using a high turnover ribbon blender. As used herein the term "powder matrix" means the combination of a topical anti-fungal agent, a silicone-coated boron nitride particulate material and/or additional excipients or preservatives. For use in the present invention, the fragrance inclusion complex desirably has a particle size of from about 10 microns to about 80 microns. More desirably the fragrance inclusion complex had a particle size of from about 10 microns to about 25 microns.

Desirably the cyclodextrin compound is betacyclodextrin compound. More desirably, the cyclodextrin compound is hydroxypropylbetacyclodextrin. One example of a suitable cyclodextrin material is a hydroxypropylbetacyclodextrin which is available under the registered trademark KLEPTOSE HP from Roquette America, Inc., having an office 1417 Exchange Street, P.O. Box 6647, Keokuk, Iowa 52632.

Suitably, the fragrance inclusion complex is present in a concentration of from about 0.8% to about 3% by weight of the body powder. More suitably, the fragrance inclusion complex is present in a concentration of from about 0.8% and about 1.5% by weight of the body powder.

In addition to the silicone coated boron nitride and the fragrance inclusion complex, the body powder may contain other excipient materials in combination with the topical anti-fungal agent that may enhance the efficacy or feel of the body powder. Suitable additional excipients include talc, kaolin clay, zinc oxide, zinc stearates, magnesium stearates, maleic acid, acrylic acid co-polymers, modified corn starch, or combinations thereof. Excipients such as talc, kaolin clay, acrylic acid co-polymers and modified corn starch assist in absorbing moisture, while excipients such zinc oxide, zinc stearates and magnesium stearates help to prevent clumping or gumming of the powder. Maleic acid and acrylic acid co-polymers can be used to regulate the pH of the powder to prevent irritation of the skin and to buffer the higher pH of talc. These excipients also contribute to the feel of the body powder as well as enhance processability of the body powder.

Desirably, the additional excipients will have a particle size of from about 10 microns and about 80 microns. More desirably, these excipients will have a particle size of from about 10 microns and about 25 microns. Advantageously, the additional excipients will have been treated to be bacteria resistant or controlled so as to inhibit the proliferation of bacteria on the skin surface. For example, an excipient may be treated with ethylene oxide to eliminate and/or inhibit proliferation of microorganisms on the particle surface.

Talc is the predominant excipient used in combination with the topical anti-fungal agent, the silicone coated boron nitride material, and the fragrance inclusion complex. Desirably, talc is present in a concentration of from about 50% to about 95% by weight of the body powder. More desirably, talc is present in a concentration of from about 75% to about 90% by weight of the body powder.

When kaolin clay is employed, it should be present in a concentration of from about 3% to about 5% by weight of the body powder. When zinc oxide is used, it should be present in a concentration of from about 5% to about 8% by weight of the body powder. When maleic acid is included, it should be present in a concentration of from about 0.3% to about 0.8% by weight of the body powder. When zinc stearate, magnesium stearate, acrylic acid co-polymers or modified corn starch are present, they should be present in a concentration of from about 0.5% to about 10% by weight of the body powder.

One modified corn starch suitable for use in the body powder is available under the registered trademark DRY FLO AF from National Starch & Chemical Company, having an office at 25 Tri-State Center, Suite 120, Lincolnshire, Ill. 60069. A suitable acrylic acid co-polymer is available under the registered trademark PEMULEN TR-2 from Noveon, Inc. having an office at 9911 Brecksville Road, Cleveland, Ohio 44141.

The body powder may also include at least one preservative compound in combination with the topical anti-fungal agent, the silicone coated boron nitride material, and the fragrance inclusion complex. Desirably, the preservative should be effective against yeast, particularly *Candida albicans*, molds, particularly *Aspergillus niger*, and bacteria, particularly *S. aureus, E. coli*, and *E cloacae*. Suitable preservative compounds include disodium ethylene diamine tetraacetic acid, methylparaben, and diazolidinyl urea. Disodium ethylene diamine tetraacetic acid also serves as a chelating agent to block the activity of bacterial ureases, lipases, proteases, and decarboxylases produced by *Klebsiella pneumoniae, Proteus mirabilus*, and *E. coli* bacteria amongst others. Other preservative compounds known to those skilled in the art may also be used.

Desirably, disodium ethylene diamine tetraacetic acid may present in a concentration of from about 0.5% and about 3% by weight of the body powder. More desirably, the disodium ethylene diamine tetraacetic acid may be present in a concentration of about 1.5% by weight of the body powder. Desirably, methylparaben may be present in a concentration of at least about 0.25% by weight of the body powder. Suitably, diazolidinyl urea (available under the trade name of GERMALL II from ISP Sutton Laboratories, having an offices at 116 Summit Avenue, P.O. Box 837, Chatham, N.J. 07928) may be present in a concentration of about 0.15% to about 0.3% by weight of the body powder.

EXAMPLE

The following example is presented to provide a more detailed understanding of the invention. The particular materials and parameters are exemplary and are not intended to limit the scope of the invention.

| Class | Compound | Percent (%) |
|---|---|---|
| Topical anti-fungal agent | Miconazole nitrate | 2 |
| Excipient | Silicone coated boron nitride powder | 3 |
| Excipient | Fragrance inclusion complex | 3 |
| Excipient | Talc | 82.7 |
| Excipient | Modified corn starch | 9 |
| Preservative | Methyl paraben | 0.3 |
| | | 100 |

While the invention has been described in conjunction with several specific embodiments, it is to be understood that many alternatives, modifications and variations will be apparent to those skilled in the art in light of the foregoing description. Accordingly, this invention is intended to embrace all such alternatives, modifications, and variations that fall within the spirit and scope of the appended claims.

I claim:

1. A body powder comprising:
a topical anti-fungal agent including miconazole nitrate present in a concentration of about 2% by weight of said body powder in combination with at least two excipients having a particle size of from about 10 microns to about 80 microns and at least one preservative compound, wherein a first of said excipients is a boron nitride particulate material being coated with a silicone compound, and a second of said excipients is a fragrance molecularly entrapped within a cyclodextrin compound, said fragrance including at least one essential oil.

2. The body powder of claim 1 wherein said essential oil is ylang ylang, coriander, grapefruit, lavender, white thyme, mandarin orange oil, tuberose, jasmine, lavadin, galbanum, rose absolute, clove leaf, eucalyptus, geraniol or a mixture thereof.

3. The body powder of claim 1 wherein said cyclodextrin compound is betacyclodextrin.

4. The body powder of claim 3 wherein said cyclodextrin compound is hydroxypropylbetacyclodextrin.

5. The body powder of claim 1 wherein said topical anti-fungal agent and said excipients are present in a dry, particulate form.

6. A body powder comprising:
miconazole nitrate anti-fungal agent present in a concentration of about 2% by weight of said body powder in combination with at least two excipients and at least two preservative compounds, wherein a first of said excipients is a boron nitride particulate material having a flat plate morphology and being present in a concentration of from about 2% to 7% by weight of said body powder, said boron nitride particulate material being coated with a silicone compound, a second of said excipients is a fragrance molecularly entrapped within a cyclodextrin compound, and said at least two preservative compounds are selected from the group consisting methyl paraben, athylene diamine tetraacetic acid, diazolidinyl urea, and combinations thereof.

7. The body powder of claim 6 further comprising a third excipient, formed from talc, kaolin clay, zinc oxide, zinc stearates, magnesium stearates, maleic acid, acrylic acid copolymers, modified corn starch, and combinations thereof.

8. A body powder comprising:
miconazole nitrate anti-fungal agent present in a concentration of about 2% by weight of said body powder in combination with at least three excipients, and at least one preservative compound, wherein a first of said excipients is a boron nitride particulate material present in a concentration of from about 2% to about 7% by weight of said body powder, said boron nitride particulate material having a flat plate morphology and being coated with a silicone compound, a second of said excipients is a fragrance molecularly entrapped within a betacyclodextrin compound, and a third of said excipients is talc, and at least one of said preservative compounds is methyl paraben.

9. The body powder of claim 8 wherein said talc is present in a concentration of from about 50% to about 95% by weight of the body powder.

10. The body powder of claim 8 wherein said silicone compound is polydimethylsiloxane or polymethylhydrogen siloxane.

11. The body powder of claim 8 wherein said fragrance is present in a concentration of between from about 0.8% to about 3% by weight of said body powder.

12. The body powder of claim 8 wherein said methyl paraben is present in a concentration of at least about 0.25% by weight of said body powder.

13. The body powder of claim 1 wherein said fragrance includes at least one essential oil that is thermostable up to at least 75° C.

14. The body powder of claim 1 wherein said fragrance includes from about 0.01% to about 1% by weight of at least one essential oil.

15. The body powder of claim 6 wherein said excipients have a particle size from about 10 microns to about 80 microns.

16. The body powder of claim 6 wherein said fragrance includes at least one essential oil selected from the group consisting of sandalwood, musk, orris root, rose, lily of the valley, bergamot, orchid, ginger, nutmeg, lumerto, rosemary, clove, chamomile, achilloa, thulasi, cedar and combinations thereof.

* * * * *

UNITED STATES PATENT AND TRADEMARK OFFICE
CERTIFICATE OF CORRECTION

PATENT NO. : 6,824,763 B2
DATED : November 30, 2004
INVENTOR(S) : JoAnn Adele Brooks It is certified that error appears in the above-identified patent and that said Letters Patent is hereby corrected as shown below:

Column 7,
Line 47, after "material" and before "being" please add:
-- having a flat plate morphology and being present in a concentration of from about 2% to about 7% by weight of said body powder, said boron nitride particulate material --.

Column 8,
Line 8, after "2% to" and before "7%" please add:
-- about --;
Line 14, after "ing" and before "methyl" please add:
-- of -- and change "athylene" to -- ethylene --;
Line 17, after "excipient," and before "talc," please change "formed from" to
-- selected from the group consisting of --.

Signed and Sealed this

Nineteenth Day of April, 2005

JON W. DUDAS
*Director of the United States Patent and Trademark Office*